US00PP10650P

United States Patent [19]

Evers

[11] Patent Number: Plant 10,650

[45] Date of Patent: Oct. 20, 1998

[54] HYBRID TEA ROSE PLANT NAMED 'TANKALCIG'

[75] Inventor: Hans-Jürgen Evers, Uetersen, Germany

[73] Assignee: Bear Creek Gardens, Inc., Medford, Oreg.

[21] Appl. No.: 986,903

[22] Filed: Dec. 8, 1997

[51] Int. Cl.[6] ..... A01H 5/00

[52] U.S. Cl. ..... Plt./21

[58] Field of Search ..... Plt./20, 21

[56] References Cited

U.S. PATENT DOCUMENTS

P.P. 7,052 10/1989 Winchel ..... Plt./21
P.P. 7,902 7/1992 Marciel ..... Plt./21

*Primary Examiner*—Howard J. Locker
*Attorney, Agent, or Firm*—Klarquist, Sparkman Campbell, Leigh & Whinston, LLP

[57] ABSTRACT

Hybrid Tea rose having bright red flowers of good petal count on long, straight stems, with moderate thorns, the plant having glossy, dark green foliage and good cut flower production.

1 Drawing Sheet

The present invention relates to a new and distinct variety of rose plant of the Hybrid Tea class which was originated by me by crossing 'TANorelav' (unpatented), with the variety 'KORlimit' (unpatented).

The primary objective of this breeding was to produce a new rose variety having the dark, glossy foliage; good cut flower production; and high petal count of the female, combined with the very long stems, low number of thorns, and bright red color of the male parent. The objective was substantially achieved, along with other desirable improvements, as evidenced by the following unique combination of characteristics that are outstanding in the new variety and that distinguish it from its parents, as well as from all other varieties of which I am aware:

1. Long, straight stems;
2. Clear, bright red flowers;
3. Glossy, dark green foliage;
4. Production of 24–26 stems per plant, per year under California greenhouse condtions;
5. Good petal count for a cut rose (30);
6. Moderate thorn production.

'TANkalcig' is a cut flower, greenhouse produced rose. Production is 24 –26 stems per plant per year with long stems, glossy, powdery mildew resistant foliage and very dark, but bright red flowers.

Asexual reproduction of this new variety by budding, as performed at Wasco, Calif., shows that the foregoing and all other characteristics and distinctions come true to form and are established and transmitted through succeeding propagation.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horitcultural Society (London) Colour Chart, except where ordinary dictionary significance of color is indicated.

Parentage:

*Seed parent*.—'TANorelav' (not patented).

*Pollen parent*.—'KORlimit' (not patented).

Classification:

*Botanical*.—*Rosa hybrida*.

*Commercial*.—Hybrid tea.

Flower

Observations made from specimens grown in a greenhouse environment at Somis, Calif. from January, 1995 to June, 1997.

Blooming habit: Continuous.

Bud:

*Size*.—1¾ inches long when the petals start to unfurl.

*Form*: The bud form is long, pointed ovoid.

*Color*: When sepals first divide, bud color is Red Group 53A. When half blown, the upper sides of the petals are Red Group 46A; and the lower sides of the petals are Red Group 53A.

*Sepals*.—Color: Green group 138B. Surface texture: Covered in fine hairs. There are three normally to heavily appendaged sepals. There are two unappendaged sepals with hairy edges.

*Receptacle*.—Color: Green Group 137D. Shape: Funnel. Size: Large 7/16" long ×3/8" wide). Surface: Smooth.

*Peduncle*.—Length: Very long (4 to 4½"). Surface: Glandular. Color: Medium green. Strength: Stiff, erect.

Bloom:

*Size*.—Large. Average open size is 4 inches.

*Borne*.—Singly.

*Stems*.—Long, strong (26"–30").

*Form*.—When first open, High centered.

*Form*.—Permanence: Retains its form to the end.

*Petalage*.—Number of petals under normal conditions: 30.

*Color*.—The upper sides of the petals are Red Group 46A. The reverse sides of the petals are Red Group 53A. The base of the petals is small, yellowish half moon at the point of attachment (⅛"×⅛"). The major color on the upper side is Red Group 46A.

*Variegations*.—None.

*Discoloration*.—The general tonality at the end of the first day: No change. At the end of the third day: No change. No change through ten days in the vase, then some discoloration through day twelve when petals collapse.

*Fragrance*.—None.

Petals:

*Texture*.—Thick.

*Shape*.—Round.

*Form*.—Tips slightly recurved.

*Arrangement*.—Imbricated with few petaloids in the center.

*Persistence*.—Drop off cleanly.

*Lastingness*.—On the plant: Long (6 –7 days). As a cut flower: Long (10 –12 days).

Reproductive parts:

*Anthers*.—Size: Large. Quantity: Many. Color: Yellow. Arrangement: Regular around styles.

*Filaments*.—Color: Red.

*Pollen*.—Color: Gold yellow.

*Styles*.—Color: Red.

*Stigmas*.—Color: Greenish white.

Plant:

*Form*.—Bush.

*Growth*.—Very vigorous. Will easily reach seven feet tall by four feet wide in the greenhouse under traditional growing techniques in one year.

Foliage:

*Number of leaflets on normal mid-stem leaves*.—5.

*Size: Large* (7" long ×5" wide).

*Quantity*.—Abundant.

*Color*.—New foliage: Upper and lower foliage is Greyed-Orange Group 176A. Old foliage: Upper — Green Group 139A. Lower — Green Group 139C.

*Shape*.—Pointed oval.

*Texture*.—Upper side: Leathery, glossy.

*Edge*.—Serrated.

*Serration*.—Single, small.

*Petiole rachis*.—Color: Green.

*Petiole underside*.—Rough, with prickles.

*Stipules*.—Long (¾"); serrated, bearded.

*Disease resistance*.—Resistant to mildew under normal growing conditions at Somis, Calif. Not tested for other diseases.

Wood:

*New wood*.—Color; Light green. Bark: Smooth.

*Old wood*.—Color: Green. Bark: Smooth.

Prickles:

*Quantity*.—On main canes from base: Ordinary. On laterals from main canes: Ordinary.

*Form*.—Medium (⅜"), hooked downward.

*Color when young*.—Red.

Small prickles:

*Quantity*.—On main stalks: None. On laterals: None.

I claim:

1. A new and distinct variety of rose plant of the hybrid tea class, substantially as herein shown and described, characterized particularly as to novelty by long, straight stems, bright red, well formed flowers, glossy, dark green foliage; good cut flower production; good petal count; and moderate thorns.

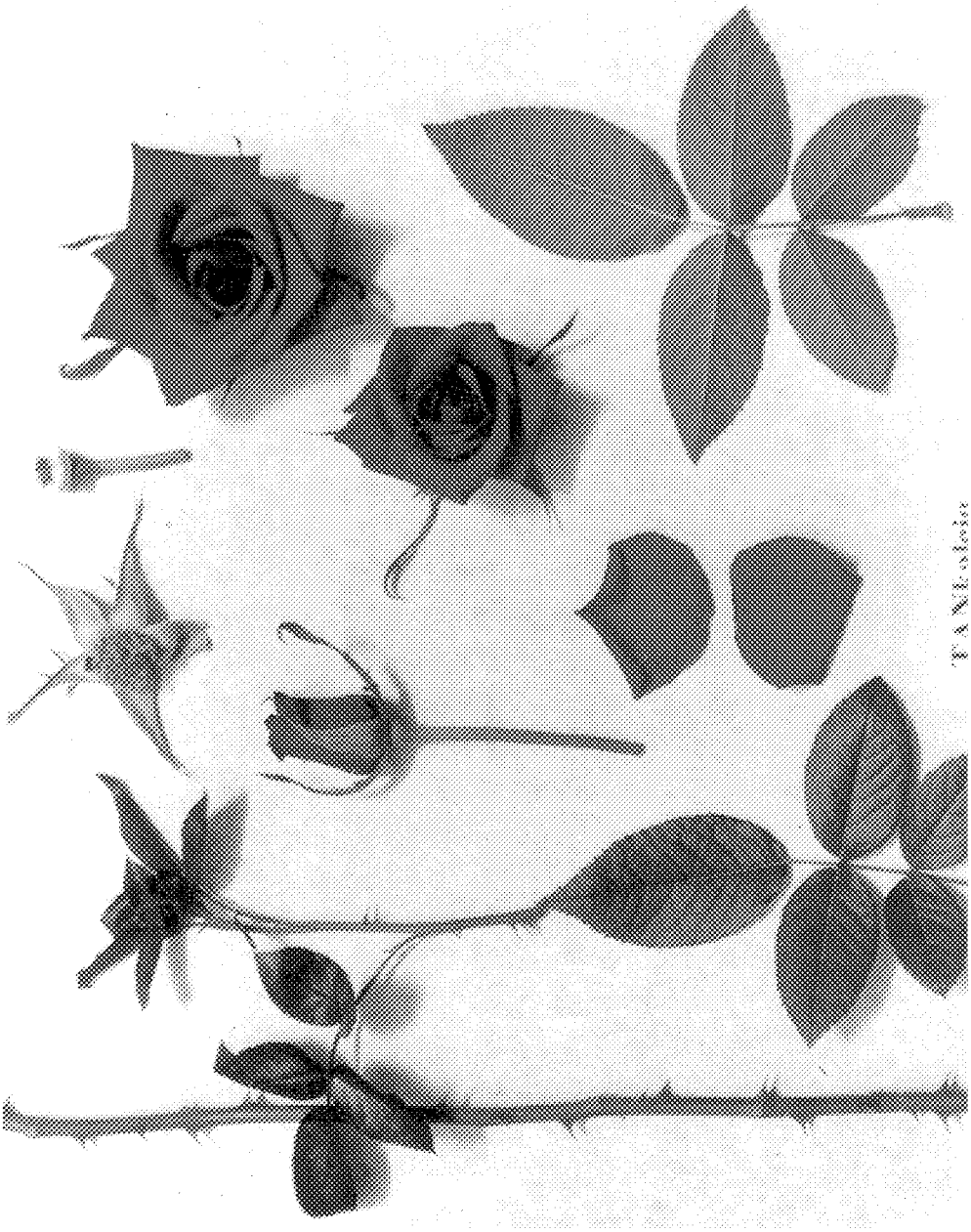

* * * * *